United States Patent [19]

Hatschek et al.

[11] Patent Number: 4,475,557
[45] Date of Patent: Oct. 9, 1984

[54] METHOD AND APPARATUS FOR PERFORMING BLOOD PRESSURE MEASUREMENTS

[75] Inventors: Rudolf Hatschek, Fribourg; Werner Bernau, Neuchâtel, both of Switzerland

[73] Assignee: Asulab S.A., Bienne, Switzerland

[21] Appl. No.: 371,367

[22] Filed: Apr. 23, 1982

[30] Foreign Application Priority Data

Apr. 24, 1981 [DE] Fed. Rep. of Germany ....... 3116387

[51] Int. Cl.³ .............................................. A61B 5/02
[52] U.S. Cl. .................................... 128/681; 128/680
[58] Field of Search ................ 128/672, 677, 680–683

[56] References Cited

U.S. PATENT DOCUMENTS

| | | | |
|---|---|---|---|
| 3,450,131 | 6/1969 | Vogt | 128/682 |
| 3,878,834 | 4/1975 | Sanderson | 128/680 |
| 3,930,494 | 1/1976 | Maurer et al. | 128/682 |
| 4,058,117 | 11/1977 | Kaspari et al. | 128/682 |
| 4,188,955 | 2/1980 | Sakamoto et al. | 128/680 |
| 4,214,589 | 7/1980 | Sakamoto et al. | 128/680 |
| 4,313,445 | 2/1982 | Georgi | 128/682 X |
| 4,356,827 | 11/1982 | Uemura et al. | 128/681 X |

*Primary Examiner*—Lee S. Cohen
*Assistant Examiner*—Angela D. Sykes
*Attorney, Agent, or Firm*—Pollock, Vande Sande & Priddy

[57] ABSTRACT

The sphygmomanometer comprises an arm band having an inflatable cuff and a microphone, and an instrument connected to the arm band, which contains the necessary pneumatic and electronic elements. By means of the microphone and an amplifier, electrical signals corresponding to the Korotkoff sounds are generated during the decompression phase, and are applied to a discriminator. At the appearance of the first and the last signals, corresponding to the Korotkoff sounds, and each having an amplitude at least equal to a threshold value $U_R$, the pressure in the cuff is measured and stored in memory as the systolic pressure and diastolic pressure respectively. During the decompression phase, the threshold value $U_R$ is first decreasing like a value proportional to the pressure in the cuff; then it increases at appearance of each signal corresponding to a Korotkoff sound and exceeding the instantaneous value of the threshold level $U_R$, after which it decreases again. This variation of the threshold value allows an exact determination of the blood pressure, eliminating in the optimum manner the parasitic signals over a large range of pressure values and in a large domain of Korotkoff sound intensities.

6 Claims, 8 Drawing Figures

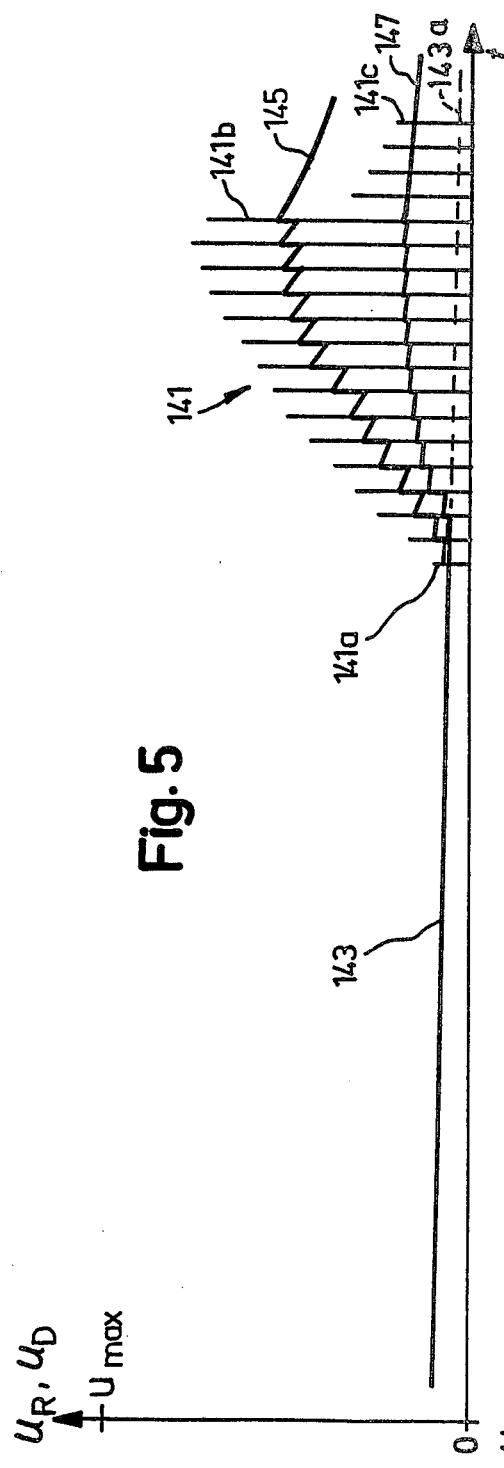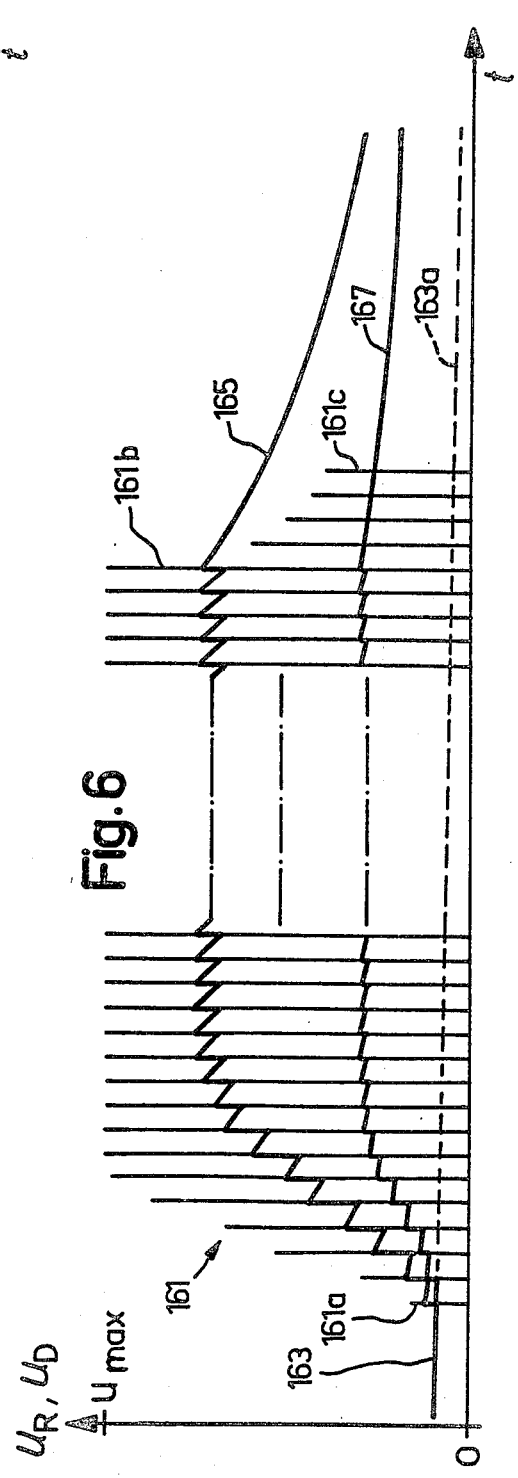

METHOD AND APPARATUS FOR PERFORMING BLOOD PRESSURE MEASUREMENTS

BACKGROUND OF THE INVENTION

The present invention concerns a method for measuring the blood pressure of a person by using an arm band mounted on a limb of the person, and having an inflatable cuff containing a gas under pressure.

The invention also concerns a sphygmomanometer for performing this method.

According to known methods the blood pressure is measured on the following manner:

the arm band, with the cuff connected to a pump, is fixed to the arm of the person;

then the pressure of gas in thee cuff is increased to a starting pressure which is greater than the probable systolic pressure of the person;

then the gas pressure in the cuff is decreased from the starting pressure to a pressure lower than the diastolic pressure of the person;

during this decrease in pressure, the sounds emitted in a zone comprising the arm band are sensed and those sounds, whose intensity is greater than a certain threshold level are validated, and the pressure in the cuff is measured when the first and the last validation of a sound occur. The pressure measured at the instant of the first validation is the systolic pressure and the pressure measured at the instant of the last validation is the diastolic pressure.

The U.S. Pat. No. 3,450,131 for example discloses a sphygmomanometer comprising a microphone for detecting the so-called Korotkoff sounds emitted by the artery of the person under examination. The microphone is connected via an amplifier to the inputs of three pass band filters, whose individual outputs are connected to a respective Schmitt trigger. These triggers produce rectangular pulses during the time intervals when the received signals are greater than a predetermined threshold. These pulses are applied to a logic circuit in order to control the recording of the pressure.

The cuff of the arm band is inflated to a pressure greater than the systolic pressure expected for the person, then the pressure in the cuff is slowly decreased.

The Korotkoff sounds produced at certain pressures are converted to electric signals by the microphone. The logic circuit at the output of the Schmitt triggers is designed so that signals having a 1000 Hz component are identified as parasite sounds, whilst signals having 40 Hz and 100 Hz components but no 1000 Hz component are identified as Korotkoff sounds. For each signal identified as a Korotkoff sound, the pressure in the cuff is measured by a pressure sensor and is recorded by a pressure recorder. The first value recorded then corresponds to the systolic pressure and the last value recorded corresponds to the diastolic pressure.

Thus in this known sphygmomanometer, the measurement of systolic and diastolic pressures is made in a manner independent of the characteristics of an individual person, and particularly in a manner independent of the absolute value of these pressures. If the Schmitt triggers are set to threshold values corresponding to average Korotkoff sound levels obtained through the evaluation of a large number of persons, it is possible that the Korotkoff sounds will be so weak that amplitude of the signals transmitted to the Schmitt triggers will not attain the said threshold levels. This leads to considerable measurement errors or may even render the measurement of blood pressure impossible. If on the other hand, Schmitt triggers are set to sufficiently low thresholds to detect extremely weak Korotkoff sounds, the distinction between the real Korotkoff sounds and the parasitic sounds will be very difficult in the case where the range of Korotkoff sounds has a medium or great intensity; this will cause numerous measurement errors.

BRIEF SUMMARY OF THE INVENTION

One object of the present invention is to propose a measurement method capable of detecting the Korotkoff sounds of feeble intensity as well and the Korotkoff sounds of strong intensity, without having an exaggerated sensitivity to parasitic sounds.

According to the invention the threshold used for the first validation of a sound is an increasing function of the pressure in the cuff.

According to a preferred embodiment of the invention, for each validation of a sound following the first validation, the threshold level is set in dependence on the intensity of the sound previously validated in such a manner that said threshold level will increase when the latter intensity increases all the other conditions being the same.

Thus the invention is principally based on the use of knowledge, obtained by research and experience, which demonstrates that an essential part of the measurement errors in known blood pressure measurement instruments is due to quantitative differences existing between individuals regarding the sound intensity of the Korotkoff sounds, and that in a same person, a strong correlation exists between the sound intensity of the Korotkoff sounds and that of certain parasitic sounds.

A comparison has been made during which the systolic and diastolic pressures measured by an apparatus operating according to the present invention were compared to values obtained by doctors using the classic method with stethoscope. The measurements were made on approximately 500 persons, among whom were patients with abnormal blood pressures, either too high or too low. A practically perfect correlation between the two measurement methods was obtained.

It is mentioned here for clarity, that in following the description and in the claims the expressions "blood pressure" and "pressure in the cuff" refer always to the excess of pressure above ambient atmospheric pressure.

BRIEF DESCRIPTION OF THE DRAWINGS

The invention will be better appreciated from the following description of an embodiment given by way of example, with reference to the accompanying drawings in which:

FIG. 5 is a diagram illustrating the variation with time of the threshold value and the signals corresponding to the Korotkoff sounds during a measurement;

FIG. 6 is a diagram corresponding to FIG. 5, but illustrating the measurement made with a patient having high blood pressure.

DETAILED DESCRIPTION OF THE PREFERRED EMBODIMENT

Figure 1:
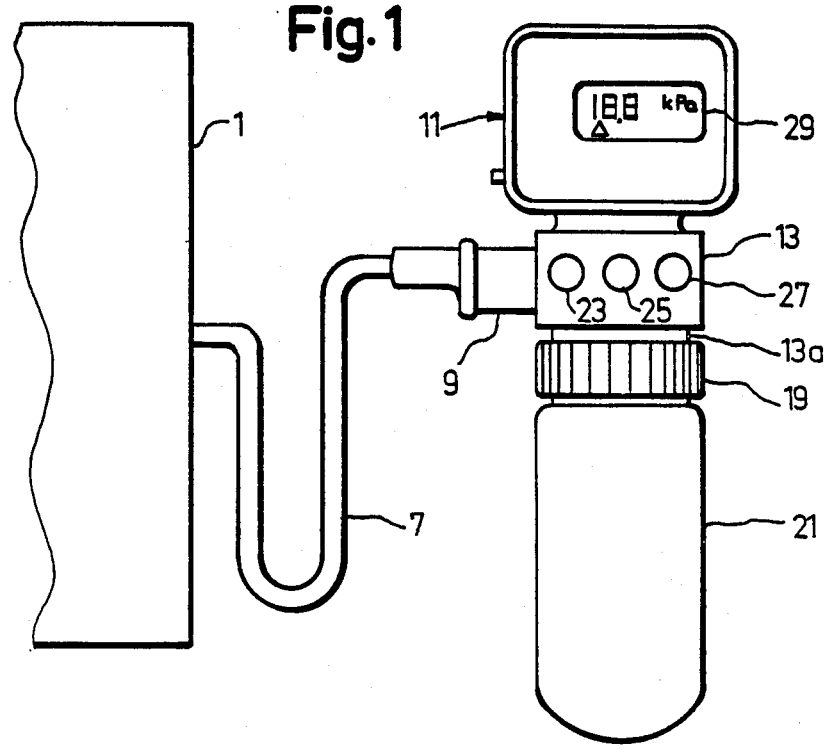
FIG. 1 is a plan view of a sphygmomanometer according to one embodiment of the invention.
Figure 2:
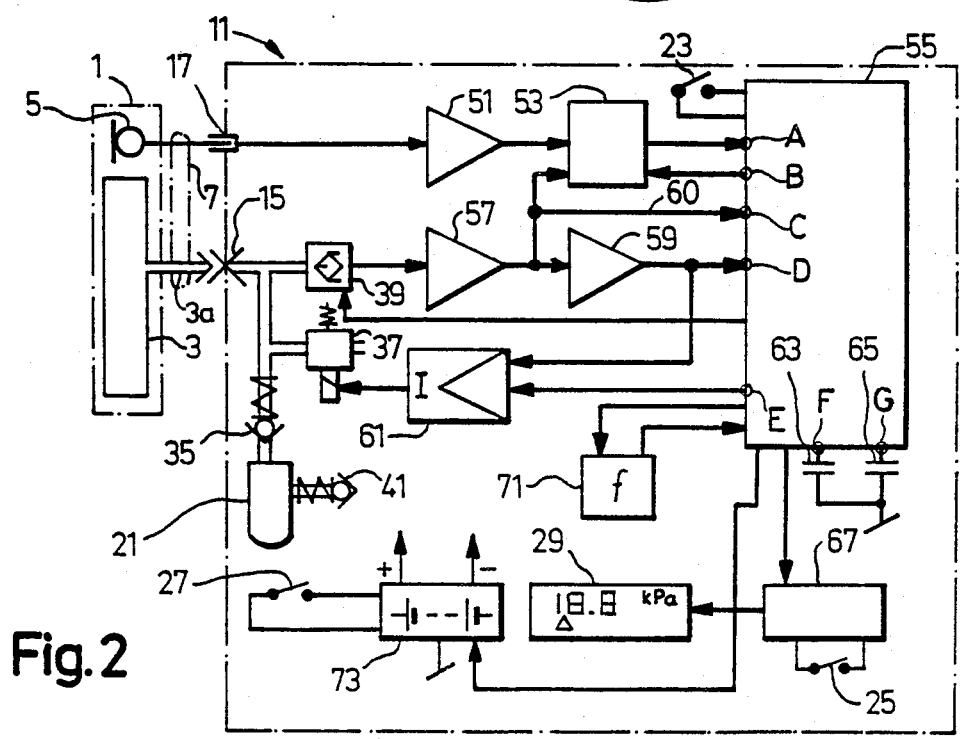
FIG. 2 is a block diagram of the sphygmomanometer shown in FIG. 1.

The sphygmomanometer shown in FIGS. 1 and 2 comprises an arm band 1 to be fitted to the arm of a person. The arm band 1 includes: (a) an airtight chamber—or cuff—3 which is deformable and is made in the form of a rubber pocket, and (b) a microphone 5. A conduit 7 is permanently connected at one end to the arm band 1; the other end is connected by a plug-in connector 9 to an instrument 11. This latter consists of a rigid case 13 on which are mounted an air connection 15 and an electrical connection 17 (see FIG. 2). The air chamber 3 is connected by a tube 3a contained in the conduit 7, to the air connection 15 and the microphone 5 is connected by a cable, contained in the conduit 7, to the electrical connection 17. The case 13 is fitted with a threaded sleeve 13a to which is attached a cylindrical hollow rubber bulb pump 21, which is removable. The apparatus also has three push buttons 23,25,27 and a digital display 29 together with various pneumatic and electronic elements contained in the case 13.

By the air connection 15, the air chamber 3 is connected by means of air passages inside the apparatus 11 through a non-return valve 35, with the pump 21, with an electrically operated pressure relief valve 37, and with a sensor 39. The pump 21 is also fitted with an air inlet and having a non-return valve 41.

The two non-return valves 35 and 41 are arranged so that when the rubber bulb of the pump 21 is squeezed in the hand and then released alternately, air is taken in the environment and the chamber 3 is inflated.

The microphone 5 is connected to the input of an amplifier-filter 51 whose output is connected to the input of a discriminator 53. The output of the discriminator 53 is connected to a controller 55.

The pressure sensor 39 produces an electrical signal constituting a measure of the pressure in the air chamber 3; this sensor consists of a piezoresistive bridge circuit which serves as a measurement transformer and which is connected to the input of an amplifier 57. The output of the amplifier 57 is connected through a differentiator circuit 59 to an input D of the controller 55 and directly by a parallel connection 60, to another input C of the controller 55. The output of the differentiator circuit 59 is also connected to one input of a regulator 61, whose output is connected to the electromagnetic actuator of the pressure relief valve 37.

The controller 55 has two other terminals F and G each of which is connected to a capacitor respectively 63 and 65 which serve as analog memories. The controller 55 is also connected to a display driver circuit 67 which contains an analog to digital converter. The circuit 67 is connected to the display 29. The push button 23 is connected to the controller 55 and the push button 25 is connected to the circuit 67. In addition a battery 73 is connected to the power inputs of the active electronic elements and to electrical ground of the instrument 11.

Figure 3:
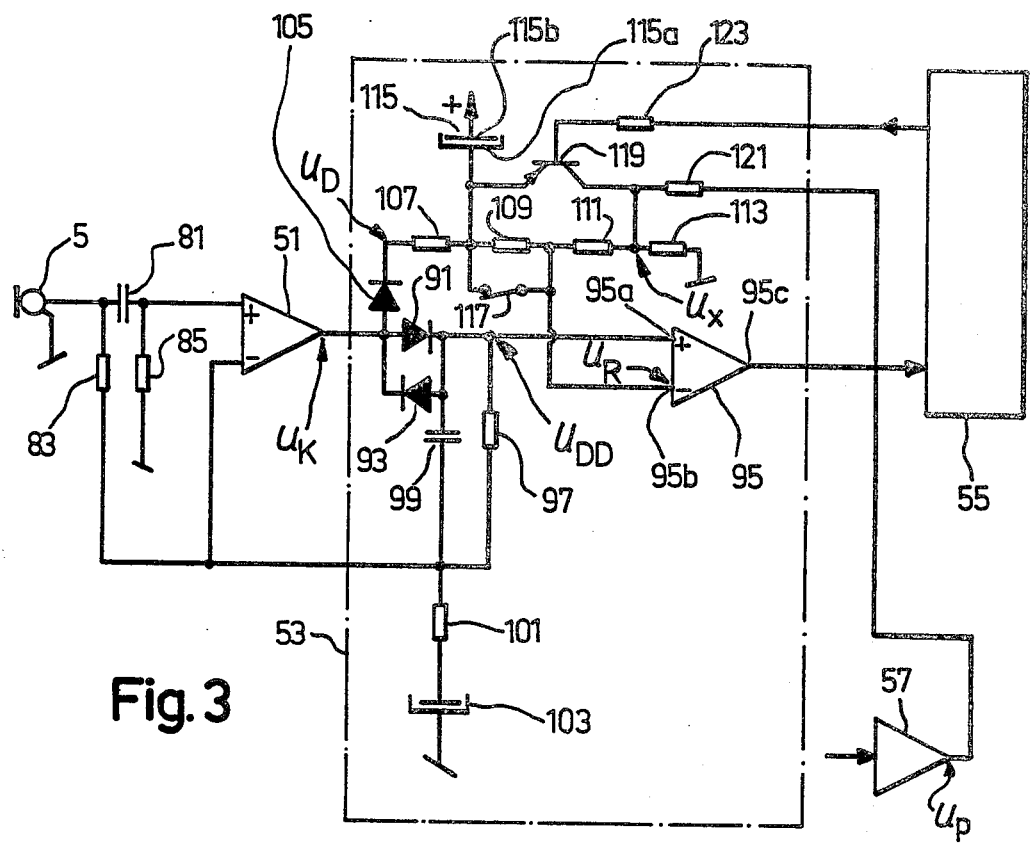
FIG. 3 shows an electronic circuit used in the sphygmomanometer of FIG. 1 for setting the value of the variable threshold.

FIG. 3 which shows with more details the circuit of the discriminator 53 and several components connected to it, is now explained.

The microphone 5 is connected to the amplifer 51 through capacitor 81; this in turn is connected to the direct (+) input of amplifier 51, and is also connected through a resistor 85 to electrical ground. In addition the microphone 5 is connected through a resistor 83 to the inverted (−) input of amplifier 51 and directly to same elements of discriminator 53.

The output of amplifier 51 is connected, through diodes 91 and 93 of discriminator 53, to the direct (+) input 95a of a differential amplifier 95, the diodes 91 and 93 are mounted in parallel with their conducting directions opposed. The input 95a is in addition connected on the one hand to the junction between the inverted (−) input of amplifier 51 and resistor 83 via a resistor 97 and a capacitor 99 connected in parallel, and on the other hand, to ground via a resistor 101 and a capacitor 103 connected in series. The output of amplifier 51 is also connected to ground by the intermediary of diode 105 and resistors 107, 109, 111 and 113 connected in series. The junction between resistors 107 and 109 is connected to one connection of a capacitor 115 whose other connection is connected to the positive connection of the battery. A manually operated switch 117 is connected in parallel with resistor 109. This switch 117 is mounted in the battery compartment of the case 13 and is accessible when the battery compartment cover is open or removed. The junction between resistors 109 and 111 is connected to the inverted (−) input 95b of amplifier 95. A switching transistor 119 has its emitter connected to connection 115a of capacitor 115, and its collector connected to the junction between resistors 111 and 113 and by the intermediary of resistor 121 to the output of amplifier 57. The base of transistor 119 is connected by the intermediary of resistor 123 to an output of controller 55. The output 95c of amplifier 95 is connected to an input of controller 55.

The capacitors 81, 99, 103 and 115 may for example have values of 3,3 μF, 10 μF, 4,7 μF and 3,3 μF. The resistors may have for example the following values: Resistor 83: 470 kΩ, Resistor 85: 2.2 MΩ, Resistor 97: 100 kΩ, Resistor 101: 1.0 kΩ, Resistor 107: 4.7 kΩ, Resistor 109: 8.8 MΩ, Resistor 111: 3.3 MΩ, Resistor 113: 2.2 kΩ, Resistor 121: 10 kΩ, Resistor 123: 22 MΩ.

Diodes 91,93 and 105 are silicon diodes and may be for example type 1 N 4148. Transistor 119 may be type BC 214.

The control circuit 55 is an integrated circuit having several switches and gates used to perform logic operations. In addition other components are connected to the integrated circuit such as capacitors used to determine time intervals.

Figure 4:
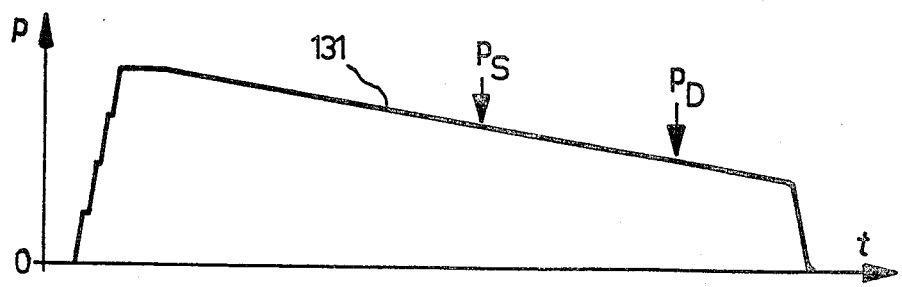
FIG. 4 shows the variation with time of the pressure in the cuff during a measurement.
Figure 7:
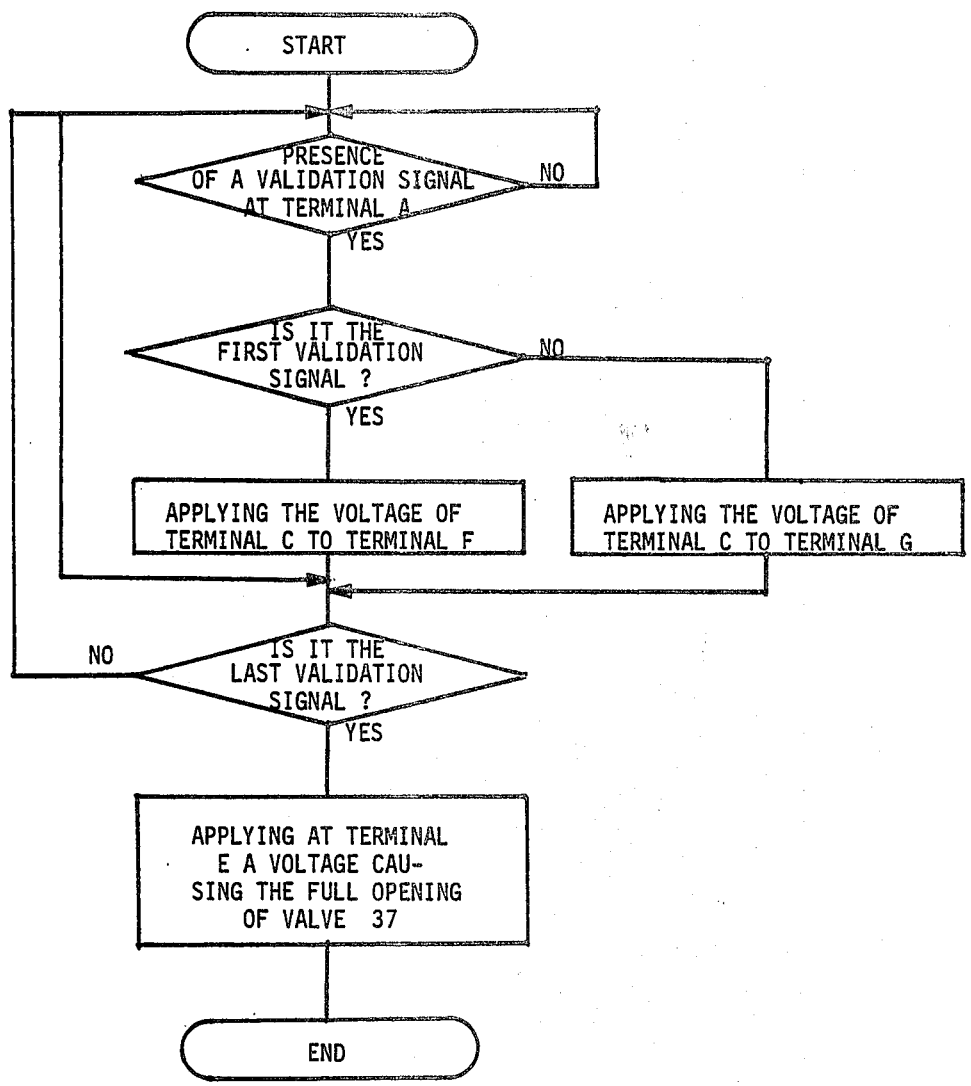
FIGS. 7 and 8 are flow charts showing the operation of a controller of the sphygmomanometer of FIG. 1.
Figure 8:
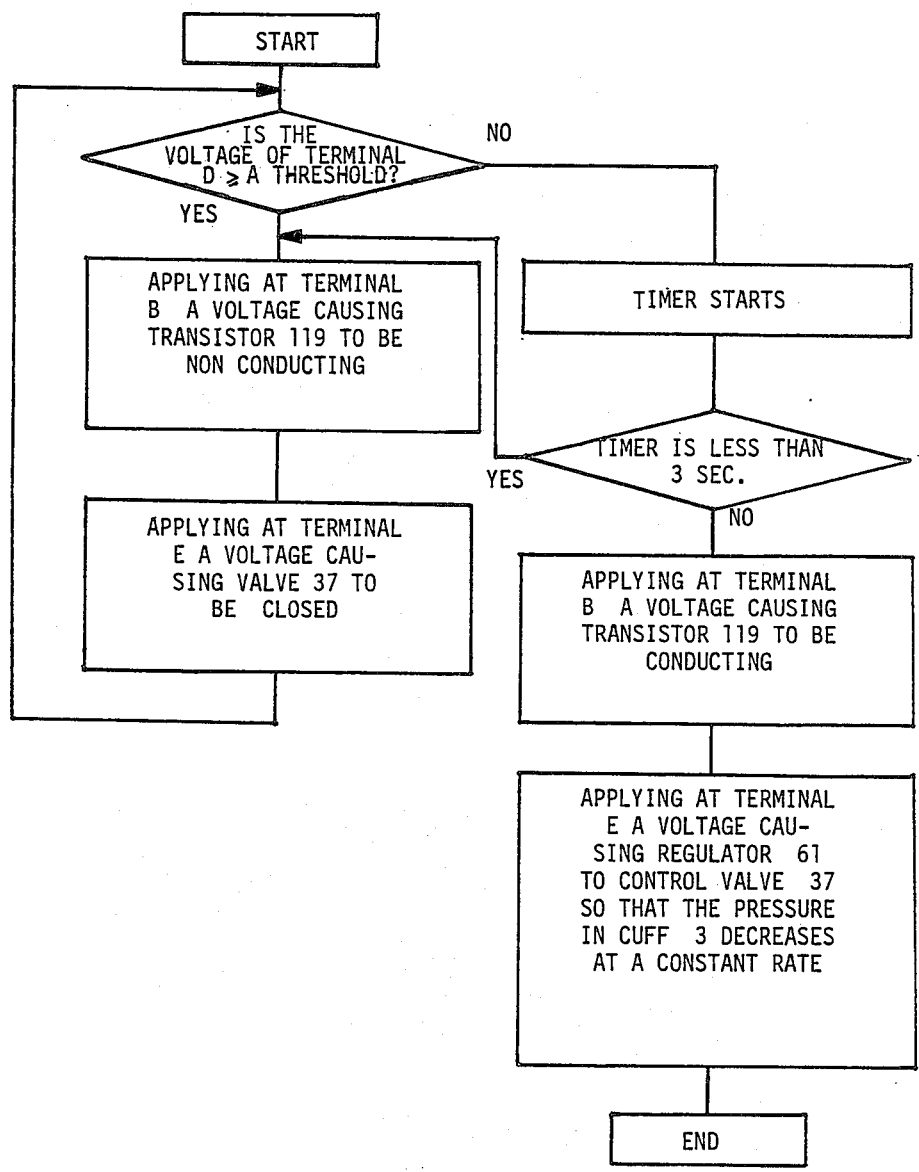

The operation of the sphygmomanometer will is now described. First the general principle of measurement will be explained using FIGS. 4, 7 and 8. In FIG. 4 curve 131 shows the evolution in time t of the pressure p in the chamber 3, then several details of FIGS. 5 and 6 will be explained.

To measure blood pressure the arm band 1 is fixed to a limb, normally an arm, of a patient. The instrument 11 to which the arm band 1 is connected is switched on by means of a brief pressure on push button 27. In the time delay which follows, during which the valve 37 is fully open and chamber 3 is at zero pressure, the pressure sensor 39 is reset to zero automatically by a reset device which is not shown. Then by manually actuating the pump 21 the pressure in the air chamber 3 is increased in steps. The valve 37 is automatically closed during the pumping by controller 55.

The valve 37 remains closed after the last pump stroke for a predetermined period, for example 3 seconds and then it is opened by the controller 55 and regulated by regulator 61, such that the pressure diminishes at a constant rate, for example 300 to 500 Pa/s. To achieve this the valve 37 must be capable of being moderated, that is to say it must have an air passage whose opening is regulated as a function of the amplitude of an electronic control signal which is supplied to the electromagnetic actuator of the said valve 37. The regulator 61 is a differential amplifier whose output is proportional to the voltage difference between terminal E of controller 55 and the output of the differentiator 59.

During a certain part of the pressure diminution phase, the blood in the artery compressed by the arm band 1, produces a set of Korotkoff sounds. Electrical signals corresponding to the Korotkoff sounds $U_K$ are thus formed and are compared in discriminator 53 with a variable threshold value $U_R$.

Whenever the amplitude of a signal $U_K$ corresponding to a Korotkoff sound is greater than the said threshold value, the discriminator 53 produces a signal hereinafter referred to as validation signal which is representative of a validated Korotkoff sound, which signal is applied to a terminal A of the controller 55. The latter, on receiving the first validation signal sends to capacitor 63, which serves as a memory, a voltage signal representative of the momentary value of pressure p which represents the systolic pressure $P_S$.

The controller 55 also, on receiving each validation signal applies to capacitor 65, serving as a memory, the voltage signal present at terminal C which is representative of the instantaneous value of p. After the detection and memorisation of the last voltage value (corresponding to a pressure p, which is the diastolic pressure) applied to capacitor 65 the controller 55, after a time lapse of for example 3 to 6 seconds, applies to regulator 61 a control signal to completely open the valve 37 allowing pressure p to fall quickly to zero.

The formation of the threshold value $U_R$ will now be described in greater detail. For each Korotkoff sound with the exception of the first sound validated by the discriminator 53, the value of the threshold $U_R$ depends essentially on the sound intensity of the last validated Korotkoff sound as explained in the following.

The low frequency electrical signals produced by the microphone 5 in response to the appearance of a Korotkoff sound are amplified by amplifier 51 which at the same time performs as a filter, due to the resistors and the capacitors which are connected to it. At the output of the amplifier 51 appears, for each Korotkoff sound, an alternating electrical signal $U_K$ of complex wave shape having a certain duration. The diode 105 operating as a rectifier passes the positive half of the waveform of the alternating voltage $U_k$ to the circuit RC formed by the resistors 107, 109, 111, 113 and the capacitor 115. At the cathode of diode 105, for each Korotkoff sound the positive half of a group of electrical waves appears. This pulsed direct current voltage will be identified as $U_D$. Shown in FIGS. 5 and 6 for each measurement are respectively a group 141 and a group 161 of Korotkoff sound signals transmitted by diode 105 over period of time t. In FIGS. 5 and 6 each Korotkoff sound is represented by a vertical segment of line whose height is equal to the peak value of the half waves passing through diode 105 as the Korotkoff sound is emitted.

The two diodes 91 and 93 connected in parallel and in opposition do not operate as a rectifier but they serve to modify the alternating voltage $U_{DD}$, transmitted by them to amplifier 95, in such a way that the positive half waves coincide as near as is possible with respect to shape, with the signals passing through diode 105. The amplifier 95 is composed of a Schmitt trigger operating as a voltage comparator delivering a rectangular pulse each time the alternating voltage $U_{DD}$ and thus also $U_D$, reaches or passes beyond the level of the threshold $U_R$.

FIGS. 5 and 6 show, together with the sets of Korotkoff sound signals 141 and 161, the segments of curves 143, 145, 147 and 163, 165, 167 respectively, which represent the variation in time of a direct current voltage transmitted to the input 95b of amplifier 95 representing the threshold value $U_R$.

As previously mentioned the pressure p in the chamber 3 diminishes linearly with respect of time during a time period starting soon after pumping has stopped.

In consequence, the D.C. voltage $U_p$ present at the output of amplifier 57, and proportional to the pressure p diminishes in a linear fashion with time. Just as long as no signal appears at the output of amplifier 51 in an initial part of the pressure dimunition phase, the voltage $U_X$ at the junction of resistors 111, 113, 121 is proportional to pressure p within a very good approximation. The threshold voltage value $U_R$ is very little influenced by the position of switch 117 during this part of the pressure diminution phase; this voltage is in particular proportional to the pressure p within a good approximation for both positions of switch 117. For the straight part of curves 143 and 163 and their prolongations 143a and 163a shown in dotted line in FIGS. 5 and 6, there are, within a good approximation the following relationships:

$$U_x = c_x p \qquad (1)$$

$$U_R = c_R P \qquad (2)$$

where $c_x$ et $c_R$ are constants similar in value and approximately equal for the two positions of switch 117.

The voltage transmitted to the input 94b of amplifier 95 which is the threshold level $U_R$ is thus a linear function of the pressure p an even proportional thereto; it therefore diminishes in a linear fashion in time before the appearance of the Korotkoff sound signals.

When the signals $U_K$ corresponding to the Korotkoff sounds or some parasites, appear at the output of amplifier 51, their influence on the threshold level $U_R$ depends on whether or not their amplitude is greater than that shown by curves 143 and 163 respectively. If the amplitude of the signals appearing at the output of amplifier 51 are not greater than that shown by curves 143 and 163 respectively the diode 105 blocks the connection between the output of the amplifier 51 and the RC circuit formed by resistors 107, 109, 111, 113, 121 and the capacitor 115. The value of the threshold $U_R$ then continues to correspond to the pressure p.

When a signal $U_K$ appears at the output of amplifier 51 and is greater than the instantaneous value of the threshold $U_R$, the diode 105 behaves temporarily as a conductor. In the RC circuit which includes capacitor 115, there is a superimposition or mixing of (a) the DC voltage $U_p$ delivered by the amplifier 57 which is proportional to pressure p, and (b) the pulsed voltage $U_D$.

In the description which follows, unless otherwise stated, the case is considered where transistor switch 119 is in a non-conducting state.

The resistors 113 and 121 are smaller by approximately 100 to 100,000 times, than the resistors 109 and 111. As a consequence, the voltage $U_x$ at the junction of the three resistors 111, 113, 121 is practically independent of the level of the voltage $U_K$ and thus dependent almost exclusively on the pressure (p) at the moment when the Korotkoff sound signals appear.

Thus the relationship (1) is also valid within a good approximation, when the Korotkoff sound signals are greater than the threshold level. Then voltage $U_x$ can be approximately represented by the dotted prolongations 143a and 163a of the curves 143 and 163.

At the appearance of each Korotkoff sound signal the voltage of which $U_K$ is greater than the threshold value $U_R$, the threshold value increases quickly tending to the peak value of the said signal $U_K$, then decreases exponentially. These rates of change in time of the threshold value are shown in FIGS. 5 and 6 by the partial curves 145, 147, 165, 167. The curves 145, 165 are those when switch 117 is closed as shown in FIG. 3, and 147, 167 are those when switch 117 is open.

When an exponential drop in the threshold value occurs after a sudden increase, the threshold value tends to a lower value $U_x$ which is variable in time and whose form is given by the dotted prolongations 143a and 163a of the partial curves 143, 163; this limit value is thus proportional to the instantaneous pressure p.

Thus the threshold value $U_R$ serving for the validation of sound signals is essentially an increasing function of the peak value of the last validated sound signal $U_K$.

The time constant with which the threshold value $U_R$ increases during sudden increases, is practically independent of the position of switch 117 and it is at most equal of 100 milliseconds; this value for example is between 6 and 30 milliseconds. On the contrary, the time constant with which the threshold diminishes after a sudden increase is strongly dependent on the position of switch 117. If switch 117 is closed, the time constant with which the threshold $U_R$ diminishes is typically comprised between 15 and 5 seconds; this value is for example 10 seconds. If switch 117 is open, the said time constant is typically of between 50 and 20 seconds; this value is for example 30 seconds. The time constant with which the threshold value $U_R$ decreases is thus equal, when switch 117 is closed, to 10% to 75% and of preferably 40% to 60% of the time constant when the switch 117 is open.

The growths of the threshold value which occur when there is a sudden increase in threshold level, are also dependent on the position of switch 117. If switch 117 is closed, the threshold values approach closer, during sudden increases, the peak values of the Korotkoff sound signals $U_K$ than when the switch is open. When there are sudden increases, the capacitor 115 should be charged by the intermediary of diode 105 and resistance 107 so that integration and smoothing occur.

When the successive Korotkoff sound signal which are greater than the threshold value $U_R$, have a constant value, as is the case in the central part of the set of Korotkoff sound signals shown in FIG. 6, the value of the threshold $U_R$ tends toward an upper limit value. This latter is at least approximately proportional to the amplitude of the Korotkoff sound signals $U_K$. If switch 117 is closed the limit value is equal to approximately 50% to 90%, for example to approximately 75% of the peak value of the corresponding Korotkoff sound signal $U_K$. If switch 117 is open, the said limit value is equal to approximately 20% to 40%, for example approximately 30% of the peak value of the corresponding Korotkoff sound signal $U_K$.

As has been already explained the systolic pressure is measured at the appearance of the first of the Korotkoff sound signals which reach or are greater than the threshold value $U_R$. This first signal is, independently of the position of switch 117, the signal 141a of the range 141 and signal 161a of the range 161.

The signals 141b and 161b corresponds to what is known as the fourth Korotkoff sound, that is to say to the sound after which the intensities of the Korotkoff sounds are greatly diminished. If the switch 117 is open, the diastolic pressure is measured when the Korotkoff sound signal 141c or 161c appears. These signals 141c, 161c correspond to that is known as the fifth Korotkoff sound, which is fairly weaker and lower in frequency than the fourth Korotkoff sound. If the switch 117 is open and all other conditions are similar, then the diastolic pressure measured with switch 117 open is less than the diastolic pressure measured with switch 117 closed.

As already mentioned in the introduction, the maximum sound intensity of the Korotkoff sounds can vary from patient to patient, the maxima of the sound level may vary by a factor ten or even more. The sound intensities depend essentially on the blood pressure of the person examined. The sound level is considerably higher for persons having a high blood pressure than for persons of medium or of low blood pressure.

The diagrams of FIGS. 5 and 6 are so positioned that the time values which are in registered relation one with the other correspond to the same pressure p in the cuff. In the diagram FIG. 6 the set of Korotkoff sounds 161 occurs in a pressure domain which is higher than the pressure domain for the set 141, shown in diagram 5. Consequently, the Korotkoff sound signals for set 161 are also in general larger than those for the set 141.

Due to the fact that the value of the threshold is modified as explained hereabove, it is achieved according to the present intention that the threshold level, when measuring systolic pressure, will be larger for a strong sound level of the Korotkoff sounds than it is for a weaker sound level. Also, when the diastolic pressure is measured, the value of the threshold $U_R$ is greater for a strong sound level of the Korotkoff sounds than is is for a weaker sound level.

Thus there is an automatic adaptation of threshold level to the different levels of sound intensity found from person to person. This facilitates blood pressure measurement with good precision for persons whose blood pressure is extremely high or extremely low, and for whom the Korotkoff sounds are extremely strong or extremely weak.

As has been shown by the preceding description a choice may be made using switch 117 whether the diastolic pressure should be measured at the fourth or fifth Korotkoff sound. If then, for example the sphygmomanometer is used by a person suffering from a blood pressure anomaly, to monitor his blood pressure, the doctor treating the patient may decide from the base of measures made using a stethoscope, if the patient should measure his diastolic blood pressure at the fourth or fifth Korotkoff sound.

The controller 55 is so designed that is does not take into account the Korotkoff sound signals $U_K$ during the pumping and a predetermined period for example one to three seconds following the pumping, so that the signals being produced during this time interval cannot cause a memorisation of a pressure p. The controller 55 is thus designed so that, during the pumping and the said predetermined period of time following the pumping, the switch formed by transistor 119 is closed. The resistors 109 and 111 are thus short-circuited and the two resistors 107 and 113 form a voltage divider for amplifier 51. Now, if capacitor 115 is removed from the circuit, this voltage divider reduces the pulsed voltage coming from diode 105 such that the voltage present at the emitter of transistor 119 will be equal to, at most 50%, for example 30%, of the voltage present at the junction between diode 105 and resistance 107.

If now the action of capacitor 115 is taken into account, when transistor 119 is conducting, this capacitor discharges very rapidly with a time constant of maximum of 30 or for example 5 to 10 milliseconds. When the switch formed by transistor 119 is closed, the parasitic signals appearing at the output of amplifier 51 do not substantially modify the threshold level $U_R$ even if they are greater than this threshold.

The sphygmomanometer described hereabove may be modified in different manner. For example the lower limit value $U_x$ which is governed by pressure p may not be made proportional to the pressure. This limit value could in effect be associated in another manner with pressure p such that this limit value decreases as the pressure decreases. This limit value could for example decrease by steps when pressure p diminishes.

While there are shown and described one preferred illustrative embodiment of the invention, it will be understood by those skilled in the art that other modifications may be made within the principles of the invention and the scope of the appended claims.

What is claimed is:

1. A sphygmomanometer comprising:
   an arm band fixable on a limb of a person, said arm band including a deformable pressurizable airtight chamber,
   means for increasing the pressure in said chamber,
   means for decreasing the pressure in said chamber,
   means responsive to said pressure for producing a signal representative of said pressure;
   means responsive to sounds produced in a zone containing said arm band for producing signals representative of the intensity of said sounds;
   providing means responsive to each said sound representative signal whose amplitude surpasses a threshold value for providing a validation signal, said providing means including determining means responsive to said pressure representative signal for determining said threshold value in dependence on the pressure in said chamber; and
   a memory;
   means responsive to: (a) said pressure representative signal and (b) said validation signals for storing in said memory the value of said pressure representative signal at the appearance of the first and of the last ones of said validation signals, respectively.

2. The sphygmomanometer of claim 1, wherein said determining means include means responsive to said sound representative signals for increasing said threshold value towards a first limit value with a first time constant during the duration of each sound representative signal which surpasses the instantaneous value of said threshold and for diminishing said threshold value towards a second limit value with a second time constant at the disappearance of said sound representative signal.

3. The sphygmomanometer of claim 1 wherein said determining means include means responsive to said sound representative signals and to a selection device for selecting a threshold value among two different values each of which are dependent on the value of at least the preceding sound representative signal which surpasses the instantaneous value of said threshold.

4. A method for measuring the blood pressure of a person, using an arm band fixed to a limb of the person, this arm band having incorporated therein a deformable chamber containing a gas at a starting pressure, this method comprising the steps of:
   reducing the pressure in said chamber from said starting pressure to a second pressure;
   sensing, during this reduction of pressure, sounds emitted in a zone at which said arm band is positioned;
   determining, for each sensed sound, an associated threshold value which is an increasing function of the pressure in the chamber;
   validating each sound whose intensity passes said associated threshold value;
   measuring the pressure in said chamber at the first and at the last validation of a sound; and
   displaying as the systolic and diastolic blood pressures respectively the pressures corresponding to said first and last validated sounds.

5. The method of claim 4, wherein said threshold value is a linear increasing function of the pressure in the chamber.

6. The method of claim 4, wherein the threshold values associated with the validated sounds other than the first validated sound further are increasing functions of the intensity of at least the sound validated immediately before.

* * * * *